（12）United States Patent
Hanson et al.

(10) Patent No.: US 6,197,978 B1
(45) Date of Patent: Mar. 6, 2001

(54) PROCESS FOR THE MANUFACTURE OF 3-N-N-DICYCLOBUTYLAMINO-8-FLUORO-3,4-DIHYDRO-2H-1-BENZOPYRAN-5-CARBOXAMIDE

(75) Inventors: Sverker Hanson; Lars Johansson; Daniel D. Sohn, all of Södertälje (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/068,284

(22) PCT Filed: Apr. 14, 1998

(86) PCT No.: PCT/SE98/00681

§ 371 Date: May 6, 1998

§ 102(e) Date: May 6, 1998

(87) PCT Pub. No.: WO98/46586

PCT Pub. Date: Oct. 22, 1998

(30) Foreign Application Priority Data

Apr. 17, 1997 (SE) .................................... 9701438

(51) Int. Cl.⁷ ........................ C07D 311/76; C07D 311/74
(52) U.S. Cl. ............................. 549/404; 549/405
(58) Field of Search ...................... 549/404, 405

(56) References Cited

U.S. PATENT DOCUMENTS 4,801,605  1/1989  Hutchison .......................... 549/405

FOREIGN PATENT DOCUMENTS 0280269  8/1988  (EP) ..................... 549/405
9511891  5/1995  (WO) ..................... 549/405

OTHER PUBLICATIONS

Eur. J. Med Chem, vol. 26, 1991, Neirabeyeh et al., "Methoxy and hydroxy derivatives of 3,4–dihydro–3–(di–n–propyl–amino)–2H–1–benzopyrans: new synthesis and dopaminergic activity", pp. 497–504.

Primary Examiner—John Kight
Assistant Examiner—Raymond Covington
(74) Attorney, Agent, or Firm—White & Case LLP

(57) ABSTRACT

A process for the manufacture of the racemic compound of the formula (I), its R-enantiomer (formula R-(I)) and its S-enantiomer (formula S-(I)),

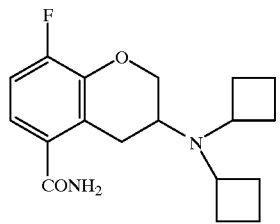
(I)

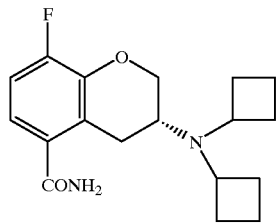

R-(I)

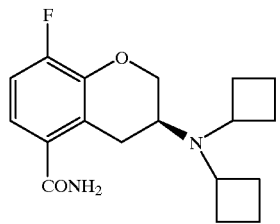

S-(I)

and pharmaceutically acceptable salts and/or solvates thereof, as well as new intermediates obtained and used in the process.

21 Claims, No Drawings

PROCESS FOR THE MANUFACTURE OF 3-N-N-DICYCLOBUTYLAMINO-8-FLUORO-3, 4-DIHYDRO-2H-1-BENZOPYRAN-5-CARBOXAMIDE

This application is the National Stage of International Application No. PCT/SE98/00681, filed Apr. 14, 1998.

FIELD OF THE INVENTION

The present invention relates to a new process for the preparation of 3-N,N-dicyclobutylamino-8-fluoro-3,4-dihydro-2H-1-benzopyran-5-carboxamide, especially (R)-3-N,N-dicyclobutylamino-8-fluoro-3,4-dihydro-2H-1-benzopyran-5-carboxamide and to new intermediates prepared therein.

BACKGROUND OF THE INVENTION (R)-3-N,N-Dicyclobutylamino-8-fluoro-3,4-dihydro-2H-1-benzopyran-5-carboxamide is disclosed in WO 95/11891 as is a process for preparing the named compound. Said process comprises a number of reaction steps. The fluorine atom is introduced into the benzopyran nucleus by selective bromination in the 8-position, followed by N,N-dibenzylation, followed by halogen-lithium exchange of the bromo compound and reaction with a suitable fluorinating agent. The obtained (R)-3-N,N-dibenzylamino-8-fluoro-5-methoxy-3,4-dihydro-2H-1-benzopyran is then subjected to debenzylation, N,N-dialkylation by reductive alkylation with cyclobutanone; demethylation; and catalytic conversion using a transition metal, carbon monoxide and an appropriate alcohol, resulting in the production of the intermediate alkyl (R)-3-N,N-dicyclobutylamino-8-fluoro-3,4-dihydro-2H-1-benzopyran-5-carboxylate. Hydrolysis of the ester to the carboxylic acid, followed by treatment of the acid with thionyl chloride gives the acid chloride which upon treatment with ammonia gives the desired (R)-3-N,N-dicyclobutylamino-8-fluoro-3,4-dihydro-2H-1-benzopyran-5-carboxamide.

The above notwithstanding there is still a need for new, more convenient and efficient processes of manufacturing (R)-3-N,N-dicyclobutylamino-8-fluoro-3,4-dihydro-2H-1-benzopyran-5-carboxamide.

The process according to the present invention for the preparation of 3-N,N-dicyclobutylamino-8-fluoro-3,4-dihydro-2H-1-benzopyran-5-carboxamide is more advantageous from a technical point of view than the process described in WO 95/11891. The claimed process employs a starting material which has the fluoro-substituent in place and thus does not require the undesirable fluorination step. The later introduction of fluorine according to the conventional process requires low temperature lithiation and reaction with an expensive, hazardous and possibly toxic fluorinating agent. Furthermore, this reaction yields a substantial amount of (R)-3-N,N-dibenzylamino-5-methoxy-3,4-dihydro-2H-1-benzopyran as a by-product which must be separated from the desired fluorinated end-product by a costly and technically difficult chromatography method. The process according to the present invention is therefore commercially more advantageous than the process known from WO 95/11891.

BRIEF DESCRIPTION OF THE INVENTION

The present invention is directed to a new process for manufacture of the racemic compound 3-N,N-dicyclobutylamino-8-fluoro-3,4-dihydro-2H-1-benzopyran-5-carboxamide having the formula (I), its R-enantiomer (formula R-(I)) and its S-enantiomer (formula S-(I)).

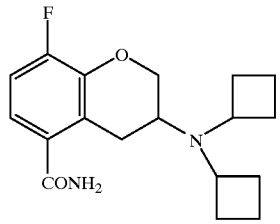

(I)

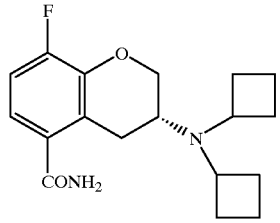

R-(I)

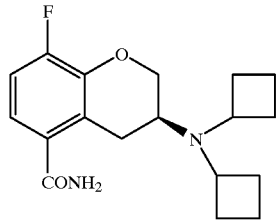

S-(I)

and pharmaceutically acceptable salts and/or solvates thereof.

DETAILED DESCRIPTION OF THE INVENTION

The new synthetic route for the manufacture of the compounds having the formulae (I), R-(I) and S-(I) is described below. The process for manufacturing (R)-3-N,N-dicyclobutylamino-8-fluoro-3,4-dihydro-2H-1-benzopyran-5-carboxamide is the main important process.

The starting material compound (II) may be purchased from, for example, Frinton Laboratories, Inc. USA. In the process according to the invention compound (III), wherein R is $C_1$–$C_4$ alkyl e.g. methyl, ethyl, n-propyl, i-propyl, n-butyl, i-butyl, t-butyl, is prepared by (a) esterification of compound (II) with a trialkyl orthoformate in an anhydrous solvent such as the corresponding alkyl alcohol. The esterification is catalyzed by an acid such as $H_2SO_4$ at a temperature between 0° C. and 100° C. The reaction may also be performed by other methods of esterification such as heating compound (II) to a temperature between 40° C. and 100° C. in an appropriate alcohol such as methanol, ethanol or propanol in the presence of an acid such as $H_2SO_4$. The carboxylic acid (III) may also be protected by other protecting groups known to a person skilled in the art, see for example: Protective Groups in Organic Synthesis; Second Edition; Theodora W. Green and Peter G. M. Wuts; John Wiley & Sons, Inc.; 1991.

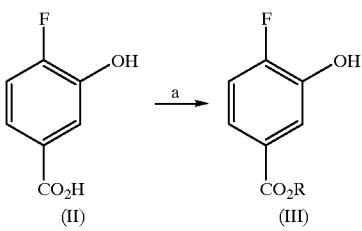

Compound (IV) is prepared by (b) alkylation of compound (III) with propargyl halides e.g. bromides, chlorides or iodides, or with propargyl alcohol activated as a sulfonate e.g. p-toluenesulfonate, in an organic solvent in the presence of a base at a temperature between 20° C. and 100° C. Examples of bases that may be used are carbonates such as sodium carbonate and potassium carbonate, or amines such as trialkylamines, e.g. triethylamine, but other possible bases will be known to a person skilled in the art. Preferably potassium carbonate is used. The organic solvent may be selected from acetone, isobutyl methyl ketone, acetonitrile and toluene, but other suitable organic solvents will be known to a person skilled in the art. Preferably acetone is used.

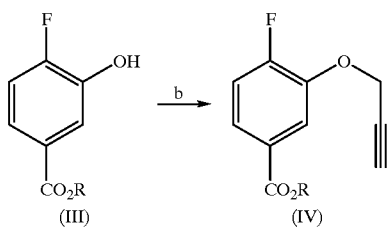

Compound (V) is prepared by (c) heating compound (IV) neat or in an appropriate aromatic solvent such as diethylaniline, dimethylaniline, diphenyl ether or in an aromatic solvent e.g. toluene or xylene, at elevated pressures, or in a saturated higher hydrocarbon, e.g. undecane or dodecane, at a temperature between 150° C. and 250° C., preferably at a temperature between 210° C. and 230° C.

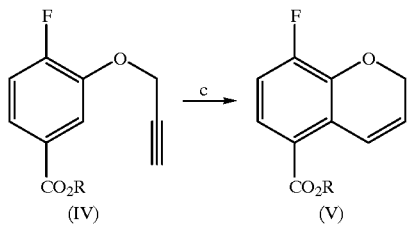

Compound (VI) is prepared by (d) hydrolysis, in the presence of a base or an acid, in a mixture of an organic solvent and water at a temperature between 20° C. and 100° C. The organic solvent may be selected from methanol, ethanol, ethylene glycol or a mixture thereof, but other suitable solvents or solvent mixtures will be known to a person skilled in the art. Preferably methanol is used. Different bases such as sodium hydroxide, potassium hydroxide or lithium hydroxide or an acid such as hydrochloric acid, sulfuric acid or trifluoromethanesulfonic acid may be used.

Compound (VII) is prepared by (e(i)) reacting compound (VI) at a temperature between 0° C. and 100° C. with oxalyl chloride or thionyl chloride with or without an organic solvent or a mixture of organic solvents present, followed by reaction with ammonia or ammonium hydroxide. The organic solvent used may be, for example, methylene chloride, ethyl acetate or toluene, or mixtures thereof. Compound (VII) may also be prepared by (e(ii)) reacting compound (V) with ammonia in an appropriate solvent at a temperature between 20° C. and 200° C. with or without pressure. The reaction can be performed in the presence or absence of catalytic amounts of acids or bases, e.g. sodium hydroxide, potassium hydroxide, lithium hydroxide, sulfuric acid, hydrochloric acid or a sulfonic acid. Other catalysts that may be used be known to a person skilled in the art. The solvent may be selected from an alcohol, water or toluene, or mixtures thereof, but other solvents will be known to a person skilled in the art. Compound (VII) may also be prepared by reacting compound (V) with a suitable amide, e.g. Formamide, in a transamidation reaction in the presence of a suitable catalyst, e.g. cyanide.

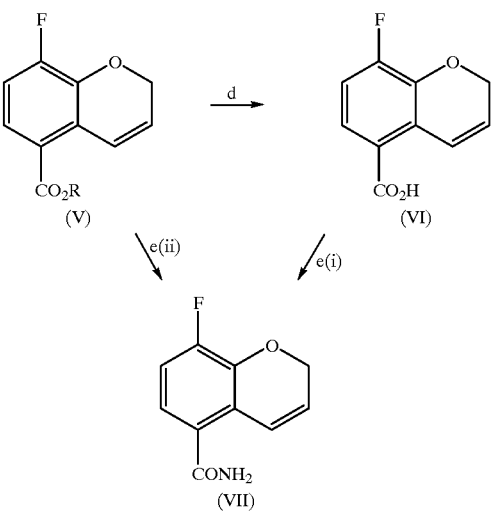

Compound (VIII) is prepared by (f) reacting compound (VII) with iodine or other iodinating agents e.g. iodine monochloride, and a nitrite salt such as silver nitrite, sodium nitrite or tetrabutylammonium nitrite in an organic solvent such as ethyl acetate, ethanol, ethylene glycol, tetrahydrofuran, mono- or diglyme or methanol or a mixture thereof in the presence or absence of water at a temperature between 0° C. and 100° C.

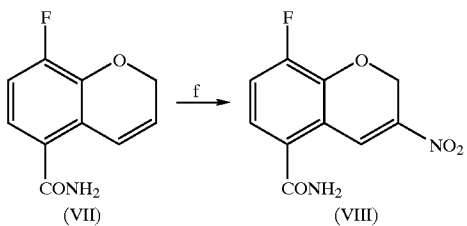

Compound (IX) is prepared by (g) reacting compound (VIII) with a reducing agent such as sodium borohydride, sodium cyanoborohydride, lithium aluminium hydride or another suitable reducing agent in the presence of ethylene glycol or silicates and an organic solvent such as ethyl acetate, methylene chloride, methanol or ethanol in the presence or absence of water and/or acetic acid at a temperature between −20° C. and 100° C., preferably at a temperature between 0° C. and 20° C.

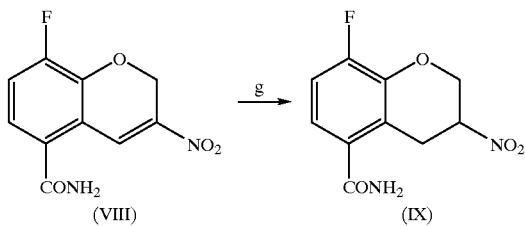

Compound (X) is prepared by (h) reduction of compound (IX) with, for example, zinc and hydrochloric acid in acetic acid at a temperature between 20° C. and 150° C., or by hydrogenation in the presence of a catalyst such as platinum, palladium or Raney nickel and hydrogen gas in an organic solvent such as tetrahydrofuran, ethyl acetate, a lower alcohol or a mixture thereof preferably in the presence of an acid, e.g. hydrochloric acid, at a temperature between −20° C. and 100° C. Other suitable reducing agents known to a person skilled in the art may also be used.

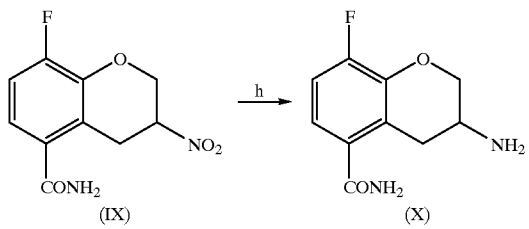

The (R)-enantiomer of compound (XI) is obtained according to known methods, such as fractional crystallization of diastereomeric salts. The diastereomeric salt is formed by (i) treatment of compound (X) with a pure enantiomer of a chiral acid such as a carboxylic acid or a sulfonic acid in an appropriate solvent such as methanol, ethanol, ethyl acetate or water but other solvents and/or solvent mixtures will be known to a person skilled in the art. The acid may be selected from pure enantiomers of tartaric acid, mandelic acid and camphanic acid but other acids will be known to a person skilled in the art. Preferably L-(+)-tartaric acid is used. The pure compound R-(XI) is obtained by treatment of the salt with a base such as sodium carbonate, potassium carbonate, calcium hydroxide, sodium hydroxide or ammonia and extracted into a suitable organic solvent e.g. diethyl ether.

The (S)-enantiomer of compound (XI) is obtained according to the procedure described for compound R-(XI) by (i) using the enantiomeric counterpart of the acid used for obtaining R-(XI). Preferably D-(−)-tartaric acid is used.

Compounds (I), R-(I) and S-(I) are prepared by (i) alkylation of compounds (X), R-(XI) and S-(XI), respectively by known methods such as reductive alkylation using cyclobutanone in the presence of a reducing agent such as sodium borohydride, sodium cyanoborohydride or a hydrogenation catalyst such as palladium or platinum in the presence of hydrogen, in an organic solvent such as methanol, ethanol, toluene, acetic acid or ethyl acetate or in a mixture thereof.

Alternatively, compounds (I), R-(I) and S-(I) may be prepared by (i) alkylation of compounds (X), R-(XI) and S-(XI), respectively with an alkylating agent such as a cyclobutyl halide or the mesylate or tosylate of cyclobutanol in a suitable organic solvent in the presence of a base and/or a catalyst. The organic solvent may be selected from acetonitrile or ethanol, but other suitable solvents will be known to a person skilled in the art. The base may be selected from sodium carbonate, potassium carbonate or triethylamine but other possible bases will be known to a person skilled in the art. The catalyst is an iodide, preferably sodium iodide.

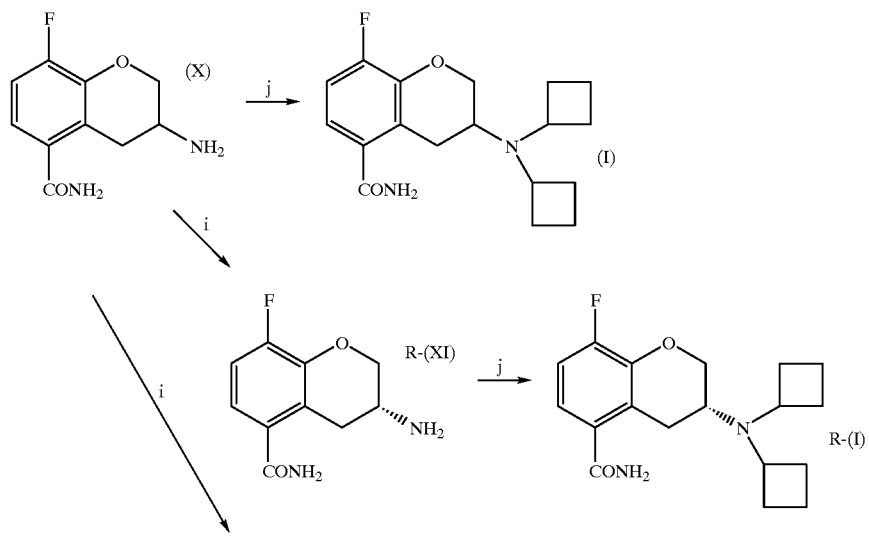

-continued

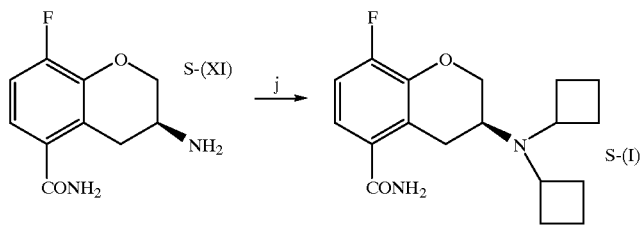

A salt of compounds (I), R-(I) and S-(I) can be prepared by conventional methods.

Intermediates

The present invention is also directed to new intermediates, namely intermediates of formulae (III) to (X), R-(XI) and S-(XI).

Especially preferred intermediates are the following:

A compound of the formula (V)

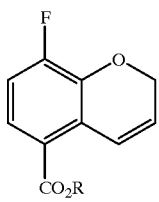

(V)

wherein R is $C_1$–$C_4$ alkyl;

a compound of the formula (VII)

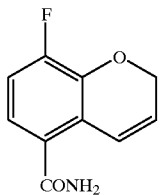

(VII)

a compound of the formula

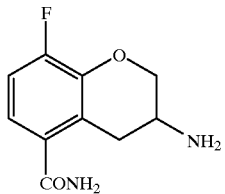

(X)

The invention will now be described in more detail by the following examples:

EXAMPLE 1

Preparation of Methyl 4-fluoro-3-hydroxybenzoate (Compound (III))

4-Fluoro-3-hydroxybenzoic acid (20.0 g, 0.13 mol) was dissolved in anhydrous methanol (160 mL), mixed with trimethyl orthoformate (25 mL) followed by the addition of concentrated $H_2SO_4$ (3 mL) and the reaction was heated to 40–55° C. overnight. Half of the solvent was removed in vacuo, the remaining solution was poured into an ice/$H_2O$ mixture and the product was extracted twice with diethyl ether. The combined ether phases were washed twice with $H_2O$, treated with a cold solution of saturated $NaHCO_3$, treated with brine, dried with $MgSO_4$, filtered, and the solvent was removed in vacuo to give 21.6 g (99% yield) of a white solid as the title compound (mp 93.5–94.5° C.). Mass spectrum (70 eV) m/z (relative intensity) 170 (44, M$^+$), 139 (100), 111 (83), 83 (83), 82 (16), 81 (11), 63 (11), 57 (24).

EXAMPLE 2

Preparation of Methyl 4-fluoro-3-propargyloxybenzoate (Compound (IV))

Methyl 4-fluoro-3-hydroxybenzoate (20.0 mL, 0.118 mol) was dissolved in anhydrous acetone (450 mL), mixed with propargyl bromide (26.2 g, 0.177 mol) followed by the addition of powdered $K_2CO_3$ (32.4 g, 0.236 mol) and the reaction mixture was stirred overnight at room temperature. The reaction was filtered and the solvent was removed in vacuo. The residue was dissolved in diethyl ether, washed 4 times with $H_2O$, treated with brine, dried with $MgSO_4$, filtered, and the solvent was removed in vacuo to give 25.5 g (100% yield) of a light peach coloured solid as the title compound (mp 60.5–61.5° C.). Mass spectrum (70 eV) m/z (relative intensity) 208 (27, M$^+$), 207 (100), 193 (22), 177 (20), 149 (50), 82 (21), 81 (10).

EXAMPLE 3

Preparation of Methyl 8-fluoro-2H-1-benzopyran-5-carboxylate (Compound (V))

Methyl 4-fluoro-3-propargyloxybenzoate (14.0 g, 67.2 mmol) was mixed with N,N-diethylaniline and the reaction was heated to 220° C. for 5 hours. The black reaction mixture was allowed to cool, dissolved in diethyl ether (600 mL) and washed with 2 M HCl in portions (1 L). The aqueous washings were re-extracted with diethyl ether, the combined ether phases were washed with $H_2O$ until neutral, treated with brine, dried with $MgSO_4$, filtered, and the solvent was removed in vacuo to give a dark brown crude residue. The crude solid was chromatographed on silica (eluent: methylene chloride/carbon tetrachloride 1:1) to give 11.9 g (85% yield) of a tannish yellow solid as the title compound (mp 73.5–74.5° C.). EIMS (70 eV) m/z (relative intensity) 208 (65, M$^+$), 207 (42), 194 (12), 193 (100), 177 (32), 149 (10), 148 (12).

EXAMPLE 4

Preparation of 8-Fluoro-2H-1-benzopyran-5-carboxylic acid (Compound (VI))

Methyl 8-fluoro-2H-1-benzopyran-5-carboxylate (7.36 g, 35.4 mmol) was dissolved in absolute ethanol (220 mL), NaOH (2.0 g, 49.6 mmol) in $H_2O$ (25 mL), was added thereto, and the reaction mixture was refluxed for 1.5 hour. The reaction mixture was cooled and the solvent was removed in vacuo. The yellow solid was dissolved in $H_2O$ (150 mL), active charcoal was added and then filtered off. The resulting light-coloured liquid was washed with diethyl ether, the aqueous solution was made acidic with 2 M HCl and the product was extracted twice with ethyl acetate. The combined organic portions were treated with brine, dried with $MgSO_4$, filtered, and the solvent was removed in vacuo to give 6.64 g (97% yield) of a yellowish solid (dried in a desiccator over $P_2O_5$) as the title compound (mp 224–226° C.). EIMS (70 eV) m/z (relative intensity) 194 (93, $M^+$), 193 (100), 149 (56), 148 (68), 120 (13), 88 (25), 75 (28), 74 (21), 60 (12).

EXAMPLE 5

Preparation of 8-Fluoro-2H-1-benzopyran-5-carboxamide (Compound (VII))

Thionyl chloride (60 mL) was added to 8-fluoro-2H-1-benzopyran-5-carboxylic acid and the solution was stirred at room temperature overnight. The excess thionyl chloride was removed in vacuo, anhydrous toluene was added and the solvent was removed in vacuo. The acid chloride was dissolved in methylene chloride (60 mL) and was added dropwise to a cooled solution (ice-bath) of concentrated ammonia (60 mL). The reaction was stirred at room temperature for 30 min. Ethyl acetate was added to the reaction mixture and the organic phase was separated. The aqueous phase was re-extracted with a methylene chloride/ethyl acetate mixture and the combined organic phases were dried with MgSO4, filtered, and the solvent was removed in vacuo to give 1.91 g (98% yield) of a white solid as the title compound (mp 194.5–195.0° C.). EIMS (70 eV) m/z (relative intensity) 193 (51, $M^+$), 192 (19), 176 (11), 175 (33), 174 (100), 149 (20), 148 (38), 101 (14), 75 (17).

EXAMPLE 6

Preparation of 8-Fluoro-3-nitro-2H-1-benzopyran-5-carboxamide (Compound (VIII))

To a solution of 8-fluoro-2H-1-benzopyran-5-carboxamide (4.46 g, 23.1 mmol) in ethyl acetate (220 mL), ethylene glycol (4.0 mL) and a solution of sodium nitrite (6.52 g, 92.4 mmol) in $H_2O$ (11 mL) were added followed by iodine (9.0 g, 34.7 mmol). The reaction mixture was refluxed for 24 hours and during this time $H_2O$ (22 mL) and ethylene glycol (4.0 mL) were added portionwise. The reaction mixture was cooled, diluted with ethyl acetate, washed with a 5% solution of $NaS_2O_3$, treated with brine, dried with $MgSO_4$, filtered, and the solvent was removed in vacuo to give a crude yellow solid. The solid was recrystallized from absolute ethanol to give 1.3 g (24% yield) of sparkly yellow crystals as the title compound (mp 227.8–228.2° C.). EIMS (70 eV) m/z (relative intensity) 238 (57, $M^+$), 221 (100), 192 (71), 191 (46), 190 (10), 148 (14), 109 (16), 94 (12).

EXAMPLE 7

Preparation of 8-Fluoro-3-nitro-3,4-dihydro-2H-1-benzopyran-5-carboxamide (Compound (IX))

8-Fluoro-3-nitro-2H-1-benzopyran-5-carboxamide (730 mg, 3.1 mmol) was slurried in chloroform (75 mL) and isopropyl alcohol (25 mL). To the stirred mixture, silica gel (2.2 g, 230–400 mesh ASTM) was added followed by powdered sodium borohydride (255 mg, 6.2 mmol) portionwise over a period of 15 min. After the addition was complete, the reaction was stirred for 20 min. and the reaction was then quenched by the addition of acetic acid (2 mL) and stirred for an additional 30 min. The insoluble material was filtered off and the solvent removed in vacuo. The residue was partitioned between ethyl acetate and water. The aqueous phase was extracted with ethyl acetate, the combined ethyl acetate phases were treated with brine, dried with $MgSO_4$, filtered, and the solvent was removed in vacuo to give 0.67 g (91% yield) of an off-white solid as the title compound (mp 191.0–191.5° C.). EIMS (70 eV) m/z (relative intensity) 240 (1, $M^+$), 195 (17), 194 (100), 193 (17), 177 (26), 151 (44), 149 (27), 148 (18), 123 (23), 103 (48), 102 (11), 101 (29), 96 (13), 95 (15), 94 (11), 88 (41), 83 (14), 77 (25), 76 (11), 75 (39), 74(23), 70 (10), 63 (11), 60 (11), 51 (17), 50 (10).

EXAMPLE 8

Preparation of 3-Amino-8-fluoro-3,4-dihydro-2H-1-benzopyran-5-carboxamide (Compound (X))

8-Fluoro-3-nitro-3,4-dihydro-2H-1-benzopyran-5-carboxamide (9.0 g, 37.5 mmol), dissolved in tetrahydrofuran (100 mL) and absolute ethanol (400 mL), was subjected to atmospheric hydrogenation conditions using Raney nickel (W-2, 9 g) at room temperature. The reaction was complete after 48 hours, at which time the catalyst was filtered off, washed with hot ethanol and the combined solvents were removed in vacuo to give 7.8 g (99% yield) of an off-white solid. A portion was recrystallized from ethyl acetate to give white crystals as the title compound (mp 187–188° C). EIMS (70 eV) m/z (relative intensity) 210 (6, $M^+$), 194 (30), 193 (100), 192 (20), 178 (12).

EXAMPLE 9

Preparation of (R)-3-Amino-8-fluoro-3,4-dihydro-2H-1-benzopyran-5-carboxamide (Compound R-(XI))

L-(+)-Tartaric acid (7 g, 47 mmol) was dissolved in a mixture of 30% ethanol in water (300 ml) and the solution heated to boiling. The racemic amine of formula (X) (8 g, 38 mmol) was added. The solution was slowly cooled to room temperature. The precipitate was filtered and washed with ethanol to give 4.7 g (65%) of slightly brown crystals (mp 175° C.). $[\alpha]^{23}D$ +67° (c 0.01, $H_2O$).

The free base was prepared by adding a $Na_2CO_3$ solution to a slurry of the tartrate in ethanol. The mixture was filtered and the solvent was removed in vacuo. The residue was dissolved in 200 ml of boiling ethyl acetate\ethanol (95:5) and filtered through celite. The solution was evaporated until the product started to crystallize, at which point it was allowed to slowly reach room temperature. The precipitate was filtered off, washed with ethyl acetate and air dried to give 1.4 g of the free base as white crystals (mp 196° C. dec.). $[\alpha]^{23}D$ −43° (c 0.005, MeOH). EIMS (70 eV) m/z (relative intensity) 210 (5, $M^+$), 194 (31), 193 (100), 192 (13), 178 (17), 148 (11).

EXAMPLE 10

Preparation of (S)-3-Amino-8-fluoro-3,4-dihydro-2H-1-benzopyran-5-carboxamide Compound S-(XM))

The (S)-enantiomer, obtained by taking the mother liquor from the above resolution and freeing the base (4 g, 19 mmol), was dissolved in methanol (20 ml) and a solution of D-(−)tartaric acid (3 g, 20 mmol) dissolved in 20 ml of methanol (20 mL) was added. The crystalline solid obtained was filtered and recrystallized from a solution of 40% ethanol in water (100 mL). 3 g of colourless crystals were obtained. (mp 173° C. dec.). $[\alpha]^{23}D$ −91° (c 0.005, $H_2O$). The free base was prepared in the same way as for the (R)-enantiomer to give 1 g of white crystals (mp 197° C. dec.). $[\alpha]^{23}D$ +44° (c 0.005, MeOH). EIMS (70 eV) m/z (relative intensity) 210 (4, M+), 194 (32), 193 (100), 192 (12), 178 (16).

EXAMPLE 11

Preparation of (R)-3-N,N-Dicyclobutylamino-8-fluoro-3,4-dihydro-2H-1-benzopyran5-carboxamide (Compound R-(I))

(R)-3-Amino-8-fluoro-3,4-dihydro-2H-1-benzopyran-5-carboxamide (0.5 g, 2.4 mmol) was dissolved in anhydrous methanol (10 mL) and to this stirred solution HOAc (140 mg, 2.4 mmol), cyclobutanone (0.5 g, 7 mmol) and NaCNBH$_3$ (0.3 g, 5 mmol) were added. The mixture was stirred at room temperature overnight. The reaction mixture was heated to 60° C. and additional amounts of cyclobutanone (0.8 g, 11 mmol), NaCNBH$_3$ (200 mg, 3.2 mmol) and HOAc (100 mg, 1.7 mmol) were added portionwise over 6 days. The solution was evaporated in vacuo, the residue was mixed with a 2 M solution of NH$_3$ and then extracted twice with ethyl acetate. The combined ethyl acetate portions were dried with Na$_2$SO$_4$, filtered, and the solvent was removed in vacuo to give the crude residue. Chromatography on silica (eluent: ethyl acetate) gave 0.5 g (82%) of the title compound as white crystals (mp 138–139° C.). $[\alpha]^{22}{}_D$ −134° (c 0.006, CH$_2$Cl$_2$). EIMS (70 eV) m/z (relative intensity) 318 (3, M+), 193 (55), 177 (11), 176 (21), 149 (18), 148 (31), 98 (54), 70 (100), 69 (40), 68 (11), 55 (40), 54 (34), 44 (17), 42 (19), 41 (59), 39 (29).

What is claimed is:

1. A process for the manufacture of the racemic compound of formula (I), its R-enantiomer (formula R-(I)) or its S-enantiomer (formula S-(I)),

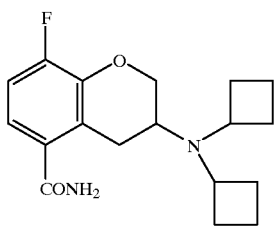

(I)

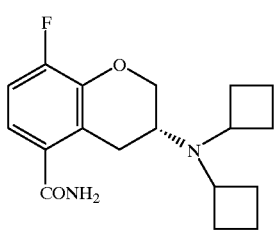

R-(I)

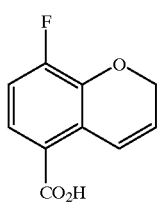

S-(I)

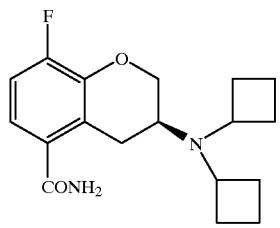

or a pharmaceutically acceptable salt and/or solvate thereof, comprising the following reaction steps a) esterification of compound (II) to yield compound (III)

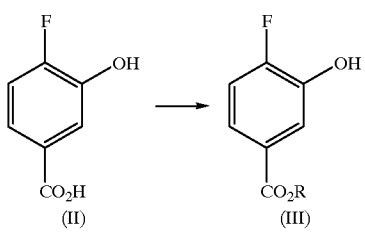

b) propargylating compound (III) in the presence of a base to yield compound (IV)

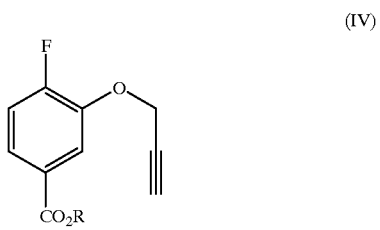

(IV)

c) heating compound (IV) to yield compound (V)

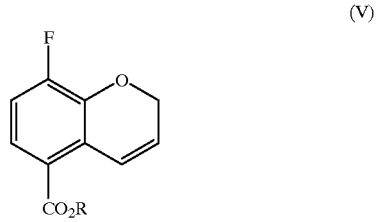

(V)

d) hydrolyzing compound (V) in the presence of a base or acid catalyst to yield compound (VI)

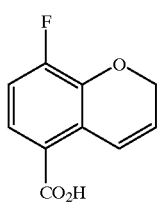

(VI)

e) either (i) reacting compound (VI) with oxalyl chloride or thionyl chloride, followed by ammonia, or (ii) reacting compound (V) with ammonia in the presence of a base or acid catalyst to yield compound (VII)

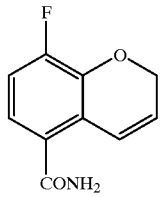
(VII)

f) reacting compound (VII) with iodine and a nitrite salt to yield compound (VIII)

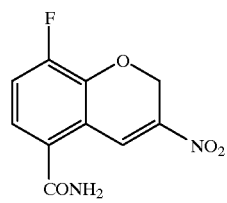
(VIII)

g) reacting compound (VIII) with a reducing agent to yield compound (IX)

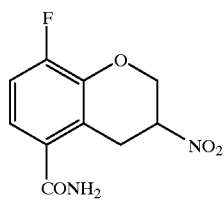
(IX)

h) reducing compound (IX) to yield compound (X)

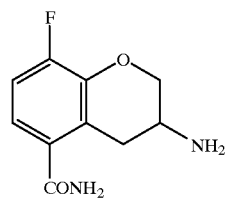
(X)

i) where the (R)- or (S)-enantiomer of compound (I) is desired, reacting compound (X) with the appropriate pure enantiomer of a chiral acid, followed by fractional crystallization and treatment of the resultant salt with a base to yield compound R-(XI) or S-(XI)

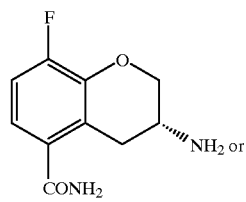
R-(XI)

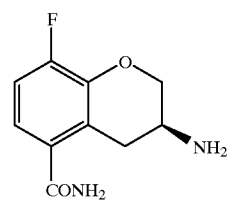
S-(XI)

j) alkylation of the compounds R-(XI) or S-(XI) to yield the compound of formulae R-(I) or S-(I), respectively, or alkylation of compound (X) to yield the racemic compound of formula (I), k) optionally treating the compound obtained in step j) in a conventional manner to yield a salt or solvate thereof.

2. A process according to claim 1, wherein step a), the esterification, is performed by using a trialkyl orthoformate.

3. A process according to claim 2, wherein the trialkyl orthoformate is trimethyl orthoformate.

4. A process according to claim 1, wherein step b), the propargylation, is performed by using a propargyl halide.

5. A process according to claim 1, wherein step c), the heating, is performed in the presence of an aromatic solvent.

6. A process according to claim 1, wherein the catalyst used in step d) is sodium hydroxide.

7. A process according to claim 1, wherein the nitrite salt used in step f) is sodium nitrite.

8. A process according to claim 1, wherein the reducing agent used in step g) is sodium borohydride.

9. A process according to claim 1, wherein L-(+)tartaric acid is the chiral acid used in step i) to yield the compound R-(XI).

10. A process according to claim 1, wherein step j), the alkylation, is performed by reductive animation of cyclobutanone in the presence of a reducing agent.

11. A process according to claim 10, wherein the reducing agent is sodium cyanoborohydride.

12. A compound of the formula R-(I) of claim 1, prepared by the process according to claim 1.

13. A compound of the formula (V)

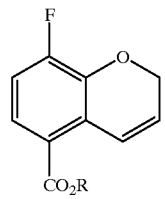
(V)

wherein R is $C_1$–$C_4$ alkyl.

14. A compound of the formula (VII)

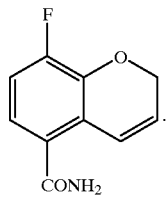

(VII)

15. A compound of the formula (X)

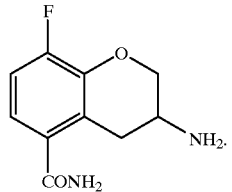

(X)

16. A compound of the formula (VIII)

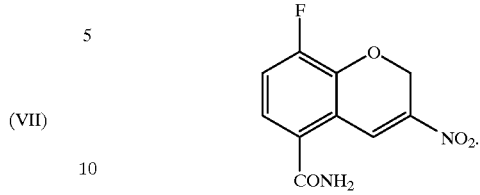

(VIII)

17. A compound of the formula (IX)

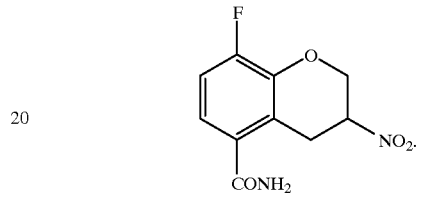

(IX)

18. A process according to claim 1, wherein step a), the esterification, is performed in an alcohol in the presence of an acid.

19. A process according to claim 1 or 4, wherein step b), the propargylation, is performed by using propargyl bromide.

20. A process according to claim 5, wherein the aromatic solvent is diethylaniline.

21. A process according to claim 5, wherein the aromatic solvent is xylene.

* * * * *

UNITED STATES PATENT AND TRADEMARK OFFICE
CERTIFICATE OF CORRECTION

Page 1 of 1

PATENT NO.    : 6,197,978
DATED         : March 6, 2001
INVENTOR(S)   : Sverker Hanson; Lars Johansson, Daniel D. Sohn It is certified that error appears in the above-identified patent and that said Letters Patent is hereby corrected as shown below:

<u>Title page,</u>
Change "3-N-N-..." to -- 3-N,N-... --;

<u>Column 14, claim 1,</u>
Line 21, change "compounds" to -- compound --; and

<u>Column 14, claim 10,</u>
Line 48, change "animation" to -- amination --.

Signed and Sealed this

Nineteenth Day of March, 2002

Attest:

JAMES E. ROGAN
Attesting Officer    Director of the United States Patent and Trademark Office